United States Patent
Faulkner et al.

(10) Patent No.: US 10,245,245 B2
(45) Date of Patent: Apr. 2, 2019

(54) COMPOSITIONS AND METHODS FOR NEUROPROTECTION AND TREATMENT OF NEURODEGENERATION

(71) Applicant: Vireo Systems, Inc., Madison, TN (US)

(72) Inventors: Mark C. Faulkner, Madison, TN (US); Donald W. Miller, Winnipeg Manitoba (CA); Grant M. Hatch, Winnipeg Manitoba (CA)

(73) Assignee: Vireo Systems, Inc., Madison, TN (US)

( * ) Notice: Subject to any disclaimer, the term of this patent is extended or adjusted under 35 U.S.C. 154(b) by 0 days.

(21) Appl. No.: 15/133,501

(22) Filed: Apr. 20, 2016

(65) Prior Publication Data

US 2016/0303061 A1  Oct. 20, 2016

Related U.S. Application Data

(60) Provisional application No. 62/150,113, filed on Apr. 20, 2015.

(51) Int. Cl.
*A61K 31/197* (2006.01)
(52) U.S. Cl.
CPC .................................. *A61K 31/197* (2013.01)
(58) Field of Classification Search
CPC .................................................. A61K 31/197
See application file for complete search history.

(56) References Cited

U.S. PATENT DOCUMENTS

| | | | |
|---|---|---|---|
| 6,706,764 B2 | 3/2004 | Kaddurah-Daouk et al. | 514/565 |
| 7,608,841 B2 | 10/2009 | Reid et al. | 250/461.1 |
| 8,026,385 B2 | 9/2011 | Miller et al. | 560/169 |
| 8,354,450 B2 | 1/2013 | Miller et al. | 514/565 |
| 2004/0242691 A1 | 12/2004 | Miller et al. | 514/565 |
| 2007/0292403 A1 | 12/2007 | Nivaggioli | 424/94.1 |
| 2010/0137255 A1 | 6/2010 | Zerangue et al. | 514/94 |
| 2011/0251280 A1 | 10/2011 | Owoc | 514/563 |
| 2013/0131175 A1 | 5/2013 | Miller et al. | 514/565 |

FOREIGN PATENT DOCUMENTS

WO    WO 2008/151249 A2    12/2008

OTHER PUBLICATIONS

U.S. Appl. No. 14/572,159, filed Dec. 16, 2014 entitled "Method and Composition for Treating Osteoarthritis".
R.K. Chaturvedi, M. Flint Beal, Free Radical Biology and Medicine, 63 (2013) pp. 1-29.
International Search Report dated Jul. 22, 2016 of corresponding International Patent Application No. PCT/US16/28357.
Huntington's Disease Society of America's 2014 Research Investor's Report: "HD Clinical Trials Update: Two of the Largest Clinical Trials Ever Conducted for HD Were Terminated in 2014", 2014.
Huntington's Disease Society of America Press Release dated Oct. 2014.
At Risk for Huntington's Disease, "Another major supplement, creatine, proven ineffective in the fight against Huntington's disease" (Oct. 30, 2014).
HD Buzz, "Largest creatine clinical trial for Huntington's disease halted after 'futility' analysis" (Oct. 29, 2014).
"Effect of creatine monohydrate on clinical progression in patients with Parkinson disease: a randomized clinical trial" (Feb. 10, 2015).
Carroll, Jeff, HD Buzz, "Does High-Dose Creatine "Slow the Onset" of Huntington's Disease?", Feb. 11, 2014.
Supplementary European Search Report dated Oct. 22, 2018 of corresponding European Patent Application No. 16783719.4.

*Primary Examiner* — James D. Anderson
(74) *Attorney, Agent, or Firm* — Bradley Arant Boult Cummings LLP

(57) ABSTRACT

Compositions for neuroprotection and treatment of neurodegeneration and methods of administering same. In particular, the present invention relates to compositions and methods for preventing or reducing neurodegeneration, such as neurodegeneration caused by Huntington's disease, including administering a daily dose of a composition including an effective amount of creatine hydrochloride to a patient in need thereof. The methods of the present invention allow for lower dosages of supplementation as compared to creatine monohydrate while retaining all of the desired biological effects of creatine supplementation.

18 Claims, 4 Drawing Sheets

Effects of Creatine Monohydrate on DGAT1 Activity in Lymphoblast Cells Taken from HD and Control Patients

| TG | WT | | | | | | HD | | | | | | |
|---|---|---|---|---|---|---|---|---|---|---|---|---|---|
| | Control | | | 1mM Creatine mono | | | Control | | | 1mM Creatine mono | | | |
| | 1 | 2 | 3 | 4 | 5 | 6 | 7 | 8 | 9 | 10 | 11 | 12 |
| DPM | 197 | 217 | 212 | 203 | 212 | 213 | 202 | 192 | 217 | 203 | 215 | 189 |
| pMol | 9.85 | 10.85 | 10.60 | 10.15 | 10.60 | 10.65 | 10.10 | 9.60 | 10.85 | 10.15 | 10.75 | 9.45 |
| Protein ug | 69.09 | 70.21 | 68.24 | 95.50 | 96.04 | 94.28 | 94.69 | 95.01 | 93.81 | 99.81 | 99.87 | 98.24 |
| pMol/mg | 98.50 | 108.50 | 106.00 | 101.50 | 106.00 | 106.50 | 101.00 | 96.00 | 108.50 | 101.50 | 107.50 | 94.50 |
| pMol/mg/min | 4.93 | 5.43 | 5.30 | 5.08 | 5.30 | 5.33 | 5.05 | 4.80 | 5.43 | 5.08 | 5.38 | 4.73 |
| AVG/STD | | 5.22 | 0.26 | | 5.23 | 0.14 | | 5.09 | 0.31 | | 5.06 | 0.33 |
| Increa/Decrease | | | | compare to wt control | 0% | P-Value 0.42667644 | compare to WT | -2% | P-Value 0.33333333 | compare to HD control | -1% | P-Value 0.46814543 |
| | | | | | | | | | | compare to WT + Cmono | -3% | P-Value 0.24935979 |

FIG. 3

Effects of Creatine Monohydrate on DGAT2 Activity in Lymphoblast Cells Taken from HD and Control Patients

| TG | WT Control | | | 1mM Creatine mono | | | AVG | | HD Control | | | 1mM Creatine mono | | | |
|---|---|---|---|---|---|---|---|---|---|---|---|---|---|---|---|
| | 1 | 2 | 3 | 4 | 5 | 6 | | 7 | 8 | 9 | 10 | 11 | 12 | | |
| DPM | 98 | 111 | 123 | 169 | 157 | 162 | | 146 | 154 | 154 | 172 | 198 | 187 | | |
| pMol | 4.90 | 5.55 | 6.15 | 8.45 | 7.85 | 8.10 | | 7.30 | 7.70 | 7.70 | 8.60 | 9.90 | 9.35 | | |
| Protein ug | 69.09 | 70.21 | 68.24 | 95.50 | 96.04 | 94.28 | | 94.69 | 95.01 | 93.81 | 99.81 | 99.87 | 98.24 | | |
| pMol/mg | 49.00 | 55.50 | 61.50 | 84.50 | 78.50 | 81.00 | | 73.00 | 77.00 | 77.00 | 86.00 | 99.00 | 93.50 | | |
| pMol/mg/min | 2.45 | 2.78 | 3.08 | 4.23 | 3.93 | 4.05 | | 3.65 | 3.85 | 3.85 | 4.30 | 4.95 | 4.68 | | |
| AVG | | 2.77 | 0.31 | | 4.07 | 0.15 | | | 3.78 | 0.12 | | 4.64 | 0.33 | | |
| Increa/Decrease | | | | compare to wt control | 47% | P-Value 0.01658051 | | compare to WT | 37% | P-Value 0.00751972 | compare to HD control | 23% | P-Value 0.01124968 | | |
| | | | | | | | | | | | compare to WT + cmono | 14% | P-Value 0.08601656 | | |

FIG. 4

COMPOSITIONS AND METHODS FOR NEUROPROTECTION AND TREATMENT OF NEURODEGENERATION

FIELD OF THE INVENTION

The present invention relates to a method for neuroprotection and treatment of neurodegeneration. In particular, the present invention relates to a method for preventing or reducing neurodegeneration, such as neurodegeneration caused by Huntington's disease, through the administration of creatine hydrochloride. The present invention also relates to compositions comprising creatine hydrochloride useful for preventing or reducing neurodegeneration.

BACKGROUND OF THE INVENTION

Neurodegeneration refers to the progressive loss of structure or function of neurons, including death of neurons. This deterioration gradually causes a loss of cognitive abilities such as memory and decision making. Neurodegeneration is a key aspect of a large number of diseases encompassed under the term, "neurodegenerative diseases." Although hundreds of different neurodegenerative disorders exist, research and attention have primarily focused on amyotrophic lateral sclerosis ("ALS"), Parkinson disease ("PD"), Huntington disease ("HD"), and Alzheimer disease ("AD"). All of these conditions lead to progressive brain damage and neurodegeneration. The causes of these neurodegenerative diseases are essentially unknown, and even when they have been identified, the mechanisms by which they initiate the disease remain speculative. At the present time, these neurodegenerative diseases are incurable.

Huntington's disease ("HD") has emerged as a model for studying neurodegenerative disease pathogenesis. HD is a hereditary brain disorder that affects muscle coordination and leads to mental decline and behavioral symptoms. The disease is caused by an autosomal dominant mutation in either of an individual's two copies of a gene called Huntingtin. This means a child of an affected person typically has a 50% chance of inheriting the disease. While there are medications that may help treat symptoms of the disease, researchers are still actively looking for a treatment that can delay the onset or slow the progression of HD. Currently, about 30,000 people in the U.S. have HD and up to 200,000 people are at risk.

Recently, dietary supplementation with creatine has been of interest for treating neurodegenerative diseases due to its anti-inflammatory and mitochondrial stabilizing effects. For example, there has been favorable rodent data to support ultra-high doses of creatine supplementation in food as a means to prevent or reduce neurodegeneration in HD mouse models. In addition, there have been some clinical trials involving the use of creatine supplementation in treating neurodegenerative disorders in HD patients. However in these clinical trials, dosages of 30 grams or more of creatine monohydrate per day were needed in order to obtain favorable results. In other words, relatively large doses of creatine monohydrate must be consumed for effective use. As toxicity for any consumable is typically related to the dose (i.e., the amount taken) and the length of the exposure, large doses of creatine monohydrate, such as those indicated, result in increased toxicity and an increased risk of undesired side effects. In addition, due to the large dosages of creatine monohydrate, patients are often required to consume the creatine monohydrate through multiple administrations per day. For example, a 30 gram daily dose of creatine monohydrate would typically mean 3-4 doses of 8-10 grams per day. As it is often difficult for patients to adhere to multiple administrations per day, this leads to compliance issues in many patients.

Accordingly, there remains a need for a more improved form of creatine with improved solubility and bioavailability characteristics that can be consumed in smaller dosage forms while also retaining the desired biological effects of creatine supplementation for treatment of neurodegeneration.

SUMMARY OF THE INVENTION

The methods and compositions of the present invention are particularly useful in the treatment of neurodegenerative disease. For example, the present invention is directed to a method for preventing or reducing neurodegeneration, including administering a daily dose of a composition including an effective amount of creatine hydrochloride to a patient in need thereof. In one embodiment, the method involves administering a daily dose of a composition including about 0.5 grams to about 20 grams of a creatine hydrochloride. In another embodiment, the effective amount comprises a daily dose of about 2 grams to about 10 grams, for example, about 2 grams to about 8 grams. The effective amount may also comprise a daily dose of more than about 0.5 grams and less than about 2 grams. The composition may be administered in the form of a pill, tablet, capsule, or gel capsule. In this aspect, the creatine hydrochloride is present in the composition in an amount of at least about 50 percent by weight. The composition may also further include creatinine, creatine monohydrate, creatine esters, or combinations thereof.

The present invention is also directed to methods of treating a neurodegenerative disease, including administering a daily dose of a composition comprising creatine hydrochloride to a patient in need thereof, wherein the daily dose comprises about 2 grams to about 12 grams, for example about 2 grams to about 10 grams or about 2 grams to about 8 grams, of creatine hydrochloride. In this aspect, the creatine hydrochloride may be present in the composition in an amount of at least about 75 percent by weight. In another embodiment, after the step of administering, levels of diacylglycerol acyltransferase 2 activity in lymphoblast cells increases by at least about 10 percent. In yet another embodiment, the daily dose of the composition is administered as a nutritional or dietary supplement or as a functional food.

Further, the present invention is directed to a method for treating Huntington's disease, including administering an effective amount of creatine hydrochloride to a patient suffering from Huntington's disease, wherein the effective amount comprises a daily dose of about 0.5 grams to about 20 grams, for example about 2 grams to about 10 grams or about 2 grams to about 8 grams. In another embodiment, the creatine hydrochloride is administered in combination with creatinine, creatine monohydrate, creatine esters, or combinations thereof. In this aspect, the creatine hydrochloride is administered in the form of a liquid, gel, or powder. In yet another embodiment, after the administering step, the spare respiratory capacity of mitochondria in lymphoblast cells increases by at least about 60 percent and the total ATP turnover of mitochondria in lymphoblast cells increases by at least about 75 percent.

BRIEF DESCRIPTION OF THE DRAWINGS

Further features and advantages of the invention can be ascertained from the following detailed description that is provided in connection with the drawing(s) described below:

FIGS. 3-4 are tabular representations of the effects of creatine monohydrate on DGAT2 activity in lymphoblast cells from HD and control patients.

DETAILED DESCRIPTION OF THE INVENTION

Figure 1:
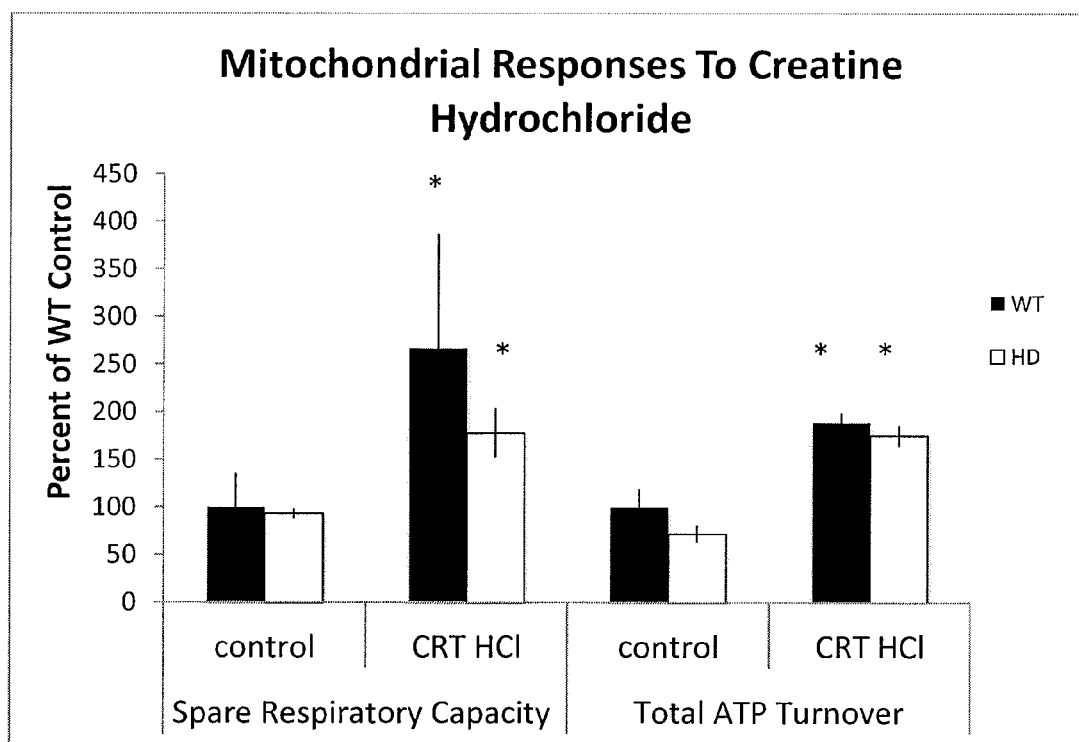
FIG. 1 is a graphical representation demonstrating the effects of creatine HCl on mitochondrial function in lymphoblasts from HD and control patients.

The present invention is directed to methods of preventing or reducing neurodegeneration in the brain through the use of compositions including creatine hydrochloride ("creatine HCl"). In one embodiment of the present invention, the creatine HCl is included in an amount effective to reduce neurodegeneration in a patient with Huntington's disease.

The pathophysiology of degenerative neurological diseases is associated with the loss of distinct populations of neurons, which are frequently interconnected. Neuronal loss or dysfunction can lead to a variety of different neurological diseases whose phenotype is dependent on the location of the neuronal loss as well as the speed of the degeneration of the neurons. A number of processes have been implicated in neurodegenerative diseases, including, for example, transcriptional dysregulation, oxidative stress, energy depletion, and mitochondrial dysfunction. Indeed, in Huntington's disease ("HD"), the mutated form of the huntingtin protein damages brain cells by interfering with cellular energy production, leading to a depletion of adenosine triphosphate ("ATP"), the molecule that powers most biological processes. As impaired cellular bioenergetics and mitochondrial dysfunction often precede onset of classical clinical presentation of HD, it has been hypothesized that altered mitochondrial function is involved in the progress of the disease. As such, it is believed therapeutic strategies which target mitochondrial dysfunction and impaired cellular bioenergetics may be useful in the treatment of neurodegenerative diseases.

Without being bound by any particular theory, it is believed that administration of creatine HCl leads to improved mitochondrial stability in patients suffering from HD. Bioenergetic deficiencies have been noted in the brain of HD patients as well as those carriers of the gene that are presymptomatic suggesting potential mitochondrial dysfunction as a contributor to the disease (R. K. Chaturvedi, M. Flint Beal, Free Radical Biology and Medicine, 63 (2013) pp. 1-29). Creatine is known to increase mitochondrial function through enhanced inner membrane stability. Functionally, the effects of creatine on mitochondria can be seen by an increase in the spare capacity of the mitochondria to perform oxidative metabolism under hypoxic conditions. For example, the present invention demonstrates that creatine HCl can increase the spare oxidative metabolism capacity in lymphoblastic cells from HD and control subjects.

Progression of disease in HD is associated with more extensive mitochondrial dysfunction (R. K. Chaturvedi, M. Flint Beal, Free Radical Biology and Medicine, 63 (2013) pp. 1-29). As mitochondria play a significant role in phospholipid metabolism, studies have also recently examined changes in lipid metabolism in HD. These studies are focusing on diacylglycerol ("DAG") pathways and the particular kinase, diacylglycerol kinase delta ("DKd"). Inhibitors of DKd, which prevent the metabolism of DAG to phosphatidic acid, were recently identified as potential therapeutic targets for HD. The present invention demonstrates that addition of creatine to lymphoblastic cells from HD patients leads to increased levels of DAG. Such effects are likely due not to inhibition of DKd, but rather enhanced production of DAG. This is a new potential pathway that may also beneficially contribute to the effects of creatine supplementation in HD patients.

Creatine HCl is a hydrochloride salt form of creatine having the following structure:

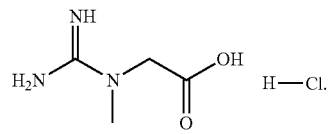

Creatine HCl has been found to possess an aqueous solubility that is at least 15 times greater than that of creatine monohydrate. Indeed, in some instances, creatine HCl has been found to possess an aqueous solubility that is at least about 50 times greater than that of creatine monohydrate.

Without being bound by any particular theory, due to its improved solubility, creatine HCl is also expected to have better oral absorption properties compared to other forms of creatine. As used herein, "bioavailability" refers to the rate and amount of a drug or supplement that reaches the systemic circulation of a patient following administration of the drug or supplement. It has been found that the relative bioavailability of creatine HCl is at least about 50 percent greater than creatine monohydrate. For example, depending on the purity of the composition including creatine HCl, the bioavailability of creatine HCl may be at least about 60 percent or greater than the bioavailability of creatine monohydrate. Indeed, in one embodiment, the composition administered according to the invention includes creatine HCl having a bioavailability of at least about 70 percent or greater relative to creatine monohydrate.

The inventors of the present invention surprisingly discovered that compositions including creatine HCl provide an effective treatment for the prevention and reduction of neurodegeneration. The terms "treatment," "treating," and "treat, are used herein to refer generally to obtaining a desired pharmacological and/or physiological effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, and includes: (a) preventing the disease or symptom from occurring in a subject which may be predisposed to the disease or symptom, but has not yet been diagnosed as having it; (b) inhibiting the disease symptom, i.e., arresting its development; or (c) relieving the disease symptom, i.e., causing regression of the disease or symptom.

For example, compositions including creatine HCl have been found to prevent or reduce neurodegeneration in patients having the huntingtin gene mutation. In particular, the compositions of the present invention have been shown to improve mitochondrial stability in cells isolated from these HD patients. Indeed, the compositions of the present invention increase both the spare respiratory capacity of mitochondria and the total ATP turnover, which in turn, prevents and reduces neurodegeneration in HD patients.

In one embodiment, administration of the compositions of the present invention has been shown to increase the spare oxidative metabolism capacity of mitochondria in cells isolated from patients having the huntingtin gene mutation. In particular, the compositions of the present invention have been found to increase the spare respiratory capacity of mitochondria in cells of these HD patients by about 50 percent or more when compared to values prior to administration. In another embodiment, the compositions of the present invention have been found to increase the spare respiratory capacity of mitochondria in cells of these HD patients by about 75 percent or more when compared to values prior to administration. In yet another embodiment, the compositions of the present invention have increased the spare respiratory capacity of mitochondria in cells of these HD patients by as much as 85 percent when compared to values prior to administration.

For instance, in studies performed on lymphoblast cells taken from both HD and non-HD patients, the in vitro administration of compositions including creatine HCl increased the spare respiratory capacity of mitochondria in lymphoblast cells of HD patients by about 60 percent or more when compared to values prior to administration. In another embodiment, in vitro administration of compositions including creatine HCl increased the spare respiratory capacity of mitochondria in lymphoblast cells taken from HD patients by about 70 percent or more when compared to values prior to administration. In still another embodiment, in vitro administration of compositions including creatine HCl increased the spare respiratory capacity of mitochondria in lymphoblast cells taken from HD patients by about 80 percent or more when compared to values prior to administration.

In this aspect, the compositions of the present invention have also been found to increase the total ATP turnover in mitochondria in cells taken from HD patients. In one embodiment, the compositions of the present invention have increased the total ATP turnover in mitochondria in cells taken from HD patients by about 80 percent or more when compared to values prior to administration. In another embodiment, the compositions of the present invention have increased the total ATP turnover in mitochondria in cells taken from HD patients by about 90 percent or more when compared to values prior to administration. In yet another embodiment, compositions of the present invention have increased the total ATP turnover in mitochondria in cells taken from HD patients by about 95 percent or more when compared to values prior to administration.

For example, in studies performed on lymphoblast cells taken from both HD and non-HD patients, in vitro administration of compositions including creatine HCl increased the total ATP turnover of mitochondria in lymphoblast cells taken from HD patients by about 75 percent or more when compared to values prior to administration. In another embodiment, in vitro administration of compositions including creatine HCl increased the total ATP turnover of mitochondria in lymphoblast cells taken from HD patients by about 85 percent or more when compared to values prior to administration. Indeed, in vitro administration of compositions including creatine HCl increased the total ATP turnover of mitochondria in lymphoblast cells taken from HD patients by about 95 percent or more when compared to values prior to administration.

The present invention has also been found to delay the onset and progression of HD. According to one embodiment of the present invention, administration of creatine HCl delays the onset and progression of disease in patients who are confirmed carriers of the HD gene mutation, but are asymptomatic. For example, administration of creatine HCl has been found to delay the onset and progression of HD at doses of creatine HCl that are substantially less than currently prescribed dosages of creatine monohydrate. In one embodiment, administration of creatine HCl at doses of about 0.5 grams to about 20 grams per day was found to delay progression of the disease. In another embodiment, administration of creatine HCl at doses of about 10 grams to about 15 grams per day was found to delay progression of HD. In yet another embodiment, administration of creatine HCl at doses of about 10 grams to about 12 grams per day was found to delay progression of HD.

In this aspect, administration of the compositions of the present invention including creatine HCl provide for increased tolerance and compliance among patients. That is, the increased bioavailability provided by the present invention decreases the amount of creatine supplementation required for beneficial effects and, in turn, reduces the likelihood of adverse side effects associated with creatine supplementation including nausea, diarrhea, and bloating. For example, in the Creatine Safety and Tolerability in Premanifest HD trial ("PRECREST"), about one-third of patients were unable to tolerate the maximum dose of creatine monohydrate (30 g daily) and 13 percent of those on placebo were unable to tolerate the maximal dose of creatine monohydrate when they switched to it. However, according to one embodiment, at least 80 percent of HD patients are able to tolerate the dosages of the creatine HCl compositions of the present invention. Indeed, at least 90 percent, preferably at least 95 percent, of HD patients are able to tolerate the dosages of the creatine HCl compositions of the present invention. Further, without being bound by any particular theory, administration of creatine HCl is believed to increase levels of diacylglycerol ("DAG") in cells isolated from HD patients. In one embodiment, exposure to creatine HCl is believed to increase diacylglycerol acyltransferase 1 ("DGAT1") and diacylglycerol acyltransferase 2 ("DGAT2") activity in cells taken from HD patients. While the present invention is described in terms of DGAT1 and DGAT2 activity, it is believed that increased activity is directly correlated with increased expression.

For example, in lymphoblast cells taken from HD patients, exposure to creatine HCl increased the activity of DGAT2 by about 10 percent or more when compared to values prior to administration. In another embodiment, exposure to creatine HCl increased the activity of DGAT2 in lymphoblast cells taken from HD patients by about 15 percent or more when compared to values prior to administration. Indeed, exposure to creatine HCl increased the activity of DGAT2 in lymphoblast cells taken from HD patients by about 20 percent or more when compared to values prior to administration.

Accordingly, one aspect of the invention involves daily administration of a composition including an effective daily dose of creatine HCl to reduce neurodegenerative effects, or slow the progression of neurodegeneration, in patients suffering from HD. In particular, the present invention contemplates a method for treating a mammal afflicted with HD that includes administering a composition including an effective amount of creatine hydrochloride to the mammal.

Compositions of the Invention

In one embodiment, the compositions for reducing and/or inhibiting neuronal degeneration according to the invention may include a compound having the structure:

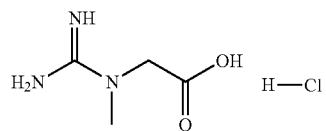

The creatine hydrochloride may be produced by a number of suitable methods including those set forth in U.S. Pat. Nos. 7,608,841, 8,026,385, and 8,354,450, the entire disclosures of which are incorporated by reference. For example, in one embodiment, the creatine HCl may be formed from the reaction of creatine monohydrate and a solvent that is infused with HCl. Starting materials useful for preparing compounds and intermediates thereof, and/or practicing methods described herein are commercially available or can be prepared by well-known synthetic methods.

Any solvent that dissolves the creatine monohydrate and precipitates creatine hydrochloride may be employed. In one embodiment, the solvent employed is an alcohol. For example, the solvent may be ethanol. Other alcohols suitable for use in the present invention include short chain alcohols selected from methanol, propanol, butanol, isopropanol, and the like. In addition, acetonitrile is contemplated for use as a suitable solvent in the context of the present invention.

The acid catalyst may be any acid catalyst that can be added to a solvent to produce a solution of dissolved HCl. Other non-limiting examples of suitable acid catalysts include acyl chlorides having the general structure: R—CO—Cl, where R is an organic radical group. For example, other acid catalysts contemplated for use with the present invention include acetyl chloride, benzoyl chloride, and (chlorocarbonyl) acetic acid. In addition, phosphorus chlorides, thionyl chloride ($SOCl_2$) are contemplated for use in accordance with the present invention. Moreover, the HCl may be generated by the reaction of sulfuric acid and sodium chloride. In one embodiment, the creatine hydrochloride is the reaction product of creatine monohydrate and acetyl chloride, dissolved in ethanol.

The yield of creatine HCl produced in each reaction can be determined by 1H-NMR analysis used for organic chemicals or other standard methods known in the art. As known to those of ordinary skill in the art, 1H-NMR uses spectroscopy and nuclear magnetic resonance technology to ascertain the structure of chemical compounds.

In one embodiment, the creatine HCl of the present invention is made as a super-saturated batch that results in yields at least about 139 percent greater than those achieved with described techniques. In order to produce a super-saturated batch of creatine HCl, a solvent and an acid catalyst are combined in a reactor that is cooled to between about 0° C. and about 20° C. Following addition of the acid catalyst, the reactor temperature is allowed to return to approximately 38° C., at which time the creatine monohydrate may be added and the reaction proceeds at a temperature between about 30° C. and about 40° C.

Preparations of the creatine HCl for use with the present invention are preferably at least about 80 percent pure, preferably at least about 95 percent pure, more preferably at least about 97 percent pure, and even more preferably at least about 99 percent pure. The term "pure" as used herein refers to the lack of impurities in the preparation. The main impurities typically detected in the composition are creatine ethyl ester hydrochloride, creatinine hydrochloride, and unreacted creatine monohydrate. The creatine HCl of the present invention may be blended in a composition with at least one other compound. In one embodiment, the at least one other compound includes a homeopathic compound, a co-medication, a nutraceutical, a plant extract, a herbal preparation, a cosmetic agent, a pharmaceutical, or combinations thereof. In another embodiment, the creatine HCl is present in a composition or blend with at least two other compounds.

For example, the creatine HCl may be combined with another ingredient in a solid dosage form. In one embodiment, the creatine HCl may be present in a composition with ethyl (α-guanido-methyl) ethanoate ("Alpha-GEE") as described in U.S. application Ser. No. 14/572,159, the entirety of which is incorporated herein by reference. In another embodiment, the creatine HCl may be present in a composition with other forms of creatine. For example, the creatine HCl may be combined with creatinine, creatine monohydrate, creatine esters, creatine pyruvate, creatine phosphate, creatine alpha-ketoglutarate, creatine citrate, and combinations thereof. In this aspect of the present invention, where creatine HCl is present in a composition or blend with at least one other compound, it is contemplated that creatine HCl will account for greater than 50 percent of the total weight of the composition. For example, the creatine HCl may be present in the composition in an amount of at least about 75 percent by weight. In another embodiment, the creatine HCl may be present in the composition in an amount of at least about 90 percent by weight. In yet another embodiment, the creatine HCl may account for less than 50 percent of the total weight of the composition. Indeed, the creatine HCl may be present in the composition in an amount of less than about 40 percent by weight.

The compositions of the present invention may further include at least one of any suitable auxiliaries including, but not limited to, diluents, binders, stabilizers, buffers, salts, lipophilic solvents, preservatives, adjuvants or the like. Pharmaceutically acceptable auxiliaries are preferred. Pharmaceutically acceptable carriers may be routinely selected that are suitable for the mode of administration, solubility and/or stability of the compound.

Pharmaceutical excipients and additives useful in the present invention may also include, but are not limited to, proteins, peptides, amino acids, lipids, and carbohydrates. Suitable protein excipients include serum albumin such as human serum albumin (HSA), recombinant human albumin (rHA), gelatin, casein, and combinations thereof. Suitable amino acid components include, but are not limited to alanine, glycine, arginine, betaine, histidine, glutamic acid, aspartic acid, cysteine, lysine, leucine, isoleucine, valine, methionine, phenylalanine, aspartame, and combinations thereof. Suitable carbohydrate excipients include, but are not limited to monosaccharides such as fructose, maltose, galactose, glucose, D-mannose, sorbose, and combinations thereof; disaccharides, such as lactose, sucrose, trehalose, cellobiose, and combinations thereof; polysaccharides, such as raffinose, melezitose, maltodextrins, dextrans, starches, and combinations thereof; and alditols, such as mannitol, xylitol, maltitol, lactitol, xylitol, sorbitol (glucitol), myoinositol, and combinations thereof.

The composition may also contain pharmaceutically acceptable carriers such as coloring agents, emulsifying agents, suspending agents, ethanol, EDTA or similar chelating agents, citrate buffer, flavoring, water, and combinations thereof. In addition, the compositions may also include a buffer or a pH adjusting agent. Suitable buffers include, but are not limited to, organic acid salts such as salts of citric acid, ascorbic acid, gluconic acid, carbonic acid, tartaric acid, succinic acid, acetic acid, or phthalic acid; Tris, tromethamine hydrochloride, or phosphate buffers.

Moreover, the compositions may include polymeric excipients/additives such as polyvinylpyrrolidones, ficolls, dextrates, polyethylene glycols, flavoring agents, anti-microbial agents, sweeteners, antioxidants, anti-static agents, surfactants, lipids, steroids, and chelating agents.

Method of Administration

In addition, the inventors discovered that based on the enhanced properties of creatine HCl, the effective dose of creatine HCl linked to the reduction of neurodegenerative effects is much less than other forms of creatine. As used herein, "effective amount" refers to the amount of the compound necessary or sufficient to treat, prevent, or ameliorate the neurodegeneration. In order to prevent or reduce neurodegeneration according to the methods of the present invention, compositions of creatine monohydrate are generally dosed in an amount of at least 30 grams per day. In contrast, an effective amount of compositions including creatine HCl according to the present invention may range from about 0.5 grams to about 20 grams per day. For example, in one embodiment, the effective amount is about 2 grams to about 12 grams per day. In another embodiment, the effective amount is about 2 grams to about 8 grams per day. In still another embodiment, the effective amount is less than about 2 grams, preferably greater than about 0.5 grams.

In comparison to creatine monohydrate, the effective amount of compositions of creatine HCl according to the present invention is at least about 50 percent less than the effective dose of creatine monohydrate. In another embodiment, the effective amount of creatine HCl is at least about 60 percent less than the effective dose of creatine monohydrate. In yet another embodiment, the effective amount of creatine HCl is at least about 70 percent less than the effective dose of creatine monohydrate. For example, the effective amount of creatine HCl is at least about 80 percent less than the effective dose of creatine monohydrate.

Accordingly, the present invention provides methods for preventing or reducing neurodegeneration caused by a neurodegenerative disease. In one embodiment, the method includes administering an effective dose of creatine HCl to a patient suffering from neurodegeneration. In another embodiment, the present invention provides methods for treating a neurodegenerative disease, such as Huntington's disease, by administering to a patient an effective amount of creatine HCl. While the effective amount can vary depending on such factors as the size and weight of the patient and the type and severity of the illness, the present invention contemplates an effective amount including a daily dose of about 0.5 grams to about 20 grams per day, preferably about 2 grams to about 12 grams per day.

In one embodiment of the present invention, the creatine HCl is provided in a liquid, gel, or powder form. For example, the creatine HCl may be in the form of a powder suitable for mixing with water or other liquids. These formulations may be added into a beverage, or the creatine HCl may be provided as an ingredient premixed in a beverage. The creatine HCl may also be administered as an elixir or as a solution formulation. In another embodiment, the creatine HCl may be encapsulated or tableted for a solid oral dosage form. For example, when treating a patient, the creatine HCl may be administered in the form of a pill, tablet, capsule, or gel capsule. In yet another embodiment, the creatine HCl may be administered in the form of a nutritional or dietary supplement. In still another embodiment, the creatine HCl may be administered in the form of a functional food, for example, a protein bar.

The creatine HCl of the present invention may be administered in conjunction with at least one other compound or pharmaceutical agent in a variety of protocols for effective treatment. In one embodiment, the at least one other compound includes a homeopathic compound, a co-medication, a nutraceutical, a plant extract, a herbal preparation, a cosmetic agent, a pharmaceutical, or combinations thereof.

The compositions of the inventions may be administered to any animal that can experience the beneficial effects of the compounds of the invention. Such animals include humans and non-humans such as pets and farm animals.

EXAMPLES

The following non-limiting examples are merely illustrative of the preferred embodiments of the present invention, and are not to be construed as limiting the invention, the scope of which is defined by the appended claims.

Example 1: Effects of Creatine HCl on Mitochondrial Function in Lymphoblast Cells from HD and Control (WT) Patients The effects of creatine HCl on mitochondrial function in lymphoblast cells taken from control (WT) and HD patients were compared. Specifically, the effects of creatine HCl (1 mM) in 24 hours on the oxygen consumption rate ("OCR") in HD and WT cells were measured. Mitochondrial function was assessed on lymphoblasts using Seahorse Analyzer. A total of 3 samples were used in both the control and HD patient groups. Values are expressed as percent of response in the WT controls receiving no creatine. *$p<0.05$ compared to respective control groups.

According to Example 1, fluorescent probes were added to measure mitochondrial potential and oxidative activity. Baseline (basal) OCR rates were measured before adding inhibitors. ATPase activity was subsequently blocked using oligomycin. The drop in OCR reflects the respiration needed to sustain ATP consumption. The remaining respiration reflects the proton leak of the mitochondria. The uncoupler, FCCP, was added. FCCP carries protons across the inner mitochondrial membrane and dissipates the electrochemical gradient (membrane potential) that drives ATP synthesis. The spare respiratory capacity and total ATP turnover (basal respiration-oligomycin insensitive respiration) of the control cells and the cells exposed to creatine HCl were calculated.

As shown in FIG. 1, administration of creatine HCl increased both the spare oxidative metabolism capacity and total ATP turnover of mitochondria in cells taken from patients suffering from HD. For example, the administration of compositions including creatine HCl increased the spare respiratory capacity of mitochondria in lymphoblast cells taken from of HD patients by about 85 percent when compared to values prior to administration. In addition, administration of creatine HCl increased the total ATP turnover of mitochondria found in lymphoblast cells taken from HD patients by about 103 percent when compared to values prior to administration.

Example 2: Effects of Creatine HCl in Patients Having HD Gene Mutation

Patients were confirmed carriers of the HD gene mutation at early stage 1 progression. Each patient was instructed to take 10 to 12 grams/day of creatine HCl. Neurological progression of disease was monitored quarterly as were full blood chemistry profiles. Assessment of neurological progression using magnetic resonance imaging (MRI) was also performed at a minimum of once a year.

Patients that had been taking creatine HCl for 3.5 years showed no progression of disease detected from either clinical neurological assessments or MRI. In addition, the patients were able to delay the onset of the disease, showing no symptoms over the 3.5 year time period.

Example 3: Diacylglycerol Acyltransferase 1 ("DGAT1") and Diacylglycerol Acyltransferase 2 ("DGAT2") Activity in Lymphoblast Cells from HD and Control (WT) Patients Exposed to Creatine Monohydrate The DGAT1 and DGAT2 activities were compared in lymphoblast cells taken from HD patients and control (WT) patients. The treated cells were exposed to 1 mM of creatine monohydrate for 24 hours.

FIGS. 3-4 demonstrate the effects of creatine monohydrate on DGAT1 and DGAT2 activity, respectively, in lymphoblast cells taken from HD patients and control patients.

| | WT Control | | | 1 mM Creatine mono | | |
|---|---|---|---|---|---|---|
| TG | 1 | 2 | 3 | 4 | 5 | 6 |
| DPM | 197 | 217 | 212 | 203 | 212 | 213 |
| pMol | 9.85 | 10.85 | 10.60 | 10.15 | 10.60 | 10.65 |
| Protein ug | 69.09 | 70.21 | 68.24 | 95.50 | 96.04 | 94.28 |
| pMol/mg | 98.50 | 108.50 | 106.00 | 101.50 | 106.00 | 106.50 |
| pMol/mg/min | 4.93 | 5.43 | 5.30 | 5.08 | 5.30 | 5.33 |
| AVG/STD | | 5.22 | 0.26 | | 5.23 | 0.14 |
| Increa/Decrease | | | | compare to wt control | 0% | P-Value 0.42667644 |

| | HD Control | | | 1 mM Creatine mono | | |
|---|---|---|---|---|---|---|
| TG | 7 | 8 | 9 | 10 | 11 | 12 |
| DPM | 202 | 192 | 217 | 203 | 215 | 189 |
| pMol | 10.10 | 9.60 | 10.85 | 10.15 | 10.75 | 9.45 |
| Protein ug | 94.69 | 95.01 | 93.81 | 99.81 | 99.87 | 98.24 |
| pMol/mg | 101.00 | 96.00 | 108.50 | 101.50 | 107.50 | 94.50 |
| pMol/mg/min | 5.05 | 4.80 | 5.43 | 5.08 | 5.38 | 4.73 |
| AVG/STD | | 5.09 | 0.31 | | 5.06 | 0.33 |
| Increa/Decrease | | | | compare to HD control | −1% | P-Value 0.46814543 |
| | compare to WT | −2% | P-Value 0.33333333 | compare to WT + Cmono | −3% | P-Value 0.24935979 |

| | WT Control | | | 1 mM Creatine mono | | |
|---|---|---|---|---|---|---|
| TG | 1 | 2 | 3 | 4 | 5 | 6 |
| DPM | 98 | 111 | 123 | 169 | 157 | 162 |
| pMol | 4.90 | 5.55 | 6.15 | 8.45 | 7.85 | 8.10 |
| Protein ug | 69.09 | 70.21 | 68.24 | 95.50 | 96.04 | 94.28 |
| pMol/mg | 49.00 | 55.50 | 61.50 | 84.50 | 78.50 | 81.00 |
| pMol/mg/min | 2.45 | 2.78 | 3.08 | 4.23 | 3.93 | 4.05 |
| AVG | | 2.77 | 0.31 | | 4.07 | 0.15 |
| Increa/Decrease | | | | compare to wt control | 47% | P-Value 0.01658051 |

| | HD Control | | | 1 mM Creatine mono | | |
|---|---|---|---|---|---|---|
| TG | 7 | 8 | 9 | 10 | 11 | 12 |
| DPM | 146 | 154 | 154 | 172 | 198 | 187 |
| pMol | 7.30 | 7.70 | 7.70 | 8.60 | 9.90 | 9.35 |
| Protein ug | 94.69 | 95.01 | 93.81 | 99.81 | 99.87 | 98.24 |
| pMol/mg | 73.00 | 77.00 | 77.00 | 86.00 | 99.00 | 93.50 |
| pMol/mg/min | 3.65 | 3.85 | 3.85 | 4.30 | 4.95 | 4.68 |

-continued

| | | | | | |
|---|---|---|---|---|---|
| AVG Increa/Decrease | | 3.78 | 0.12 | 4.64 compare to HD control | 0.33 P-Value 0.01124968 |
| | compare to WT | 37% | P-Value 0.00751972 | 14% compare to WT + cmono | P-Value 0.08501656 |

Figure 2:
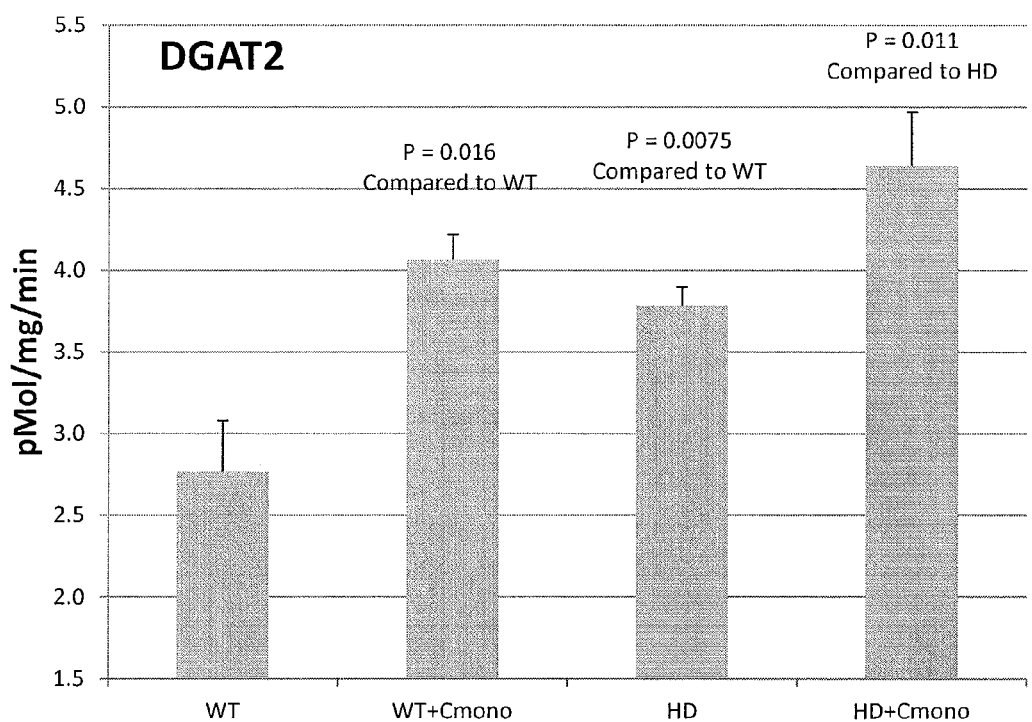
FIG. 2 is a graphical representation comparing the effects of creatine monohydrate on diacylglycerol acyltransferase 2 ("DGAT2") activity in lymphoblast cells from HD and control patients.

While there was no significant increase in DGAT1 activity after 24 hours, exposure to creatine monohydrate resulted in increased DGAT2 activity in both HD and WT cells. As shown in FIG. 2 and FIG. 4, while DGAT2 basal activity was significantly greater in HD cells, creatine exposure at 1 mM significantly increased activity in both HD and WT. For example, exposure of creatine monohydrate to lymphoblastic cells from HD patients increased the activity of DGAT2 by about 23 percent when compared to values prior to exposure. Indeed, exposure to creatine monohydrate increased the activity of DGAT2 by about 0.86 pMol/mg/min in lymphoblastic cells taken from HD patients.

Example 4 (Prophetic): DGAT2 Activity in Lymphoblast Cells from HD and Control (WT) Patients Exposed to Creatine HCl The DGAT2 activity is compared in lymphoblast cells taken from HD patients and control (WT) patients. The treated cells are exposed to 1 mM of creatine HCl for 24 hours.

In lymphoblast cells taken from HD patients, exposure to creatine HCl after 24 hours results in increased DGAT2 activity. Specifically, in lymphoblast cells taken from HD patients, exposure to creatine HCl at 1 mM results in an increase of about 20 percent or more in DGAT2 activity. That is, exposure to creatine HCl at 1 mM increases the activity of DGAT2 by about 0.85 pMol/mg/min in lymphoblastic cells from HD patients.

Although the present invention has been described with reference to particular embodiments, it will be understood to those skilled in the art that the invention is capable of a variety of alternative embodiments within the spirit of the appended claims. For example, the present invention is also contemplated for use with numerous other neurodegenerative diseases including, but not limited to, amyotrophic lateral sclerosis, Parkinson's disease, Alzheimer's disease, and prion diseases.

What is claimed is:

1. A method for preventing or reducing neurodegeneration in a human having the huntingtin gene mutation, comprising:
    administering to the human an effective amount of a composition comprising creatine hydrochloride, wherein the effective amount comprises a daily dose of creatine hydrochloride of about 2 grams to about 12 grams.

2. The method of claim 1, wherein the creatine hydrochloride is present in the composition in an amount of at least about 50 percent by weight of the composition.

3. The method of claim 1, wherein the composition further comprises creatinine.

4. The method of claim 1, wherein the composition is administered in the form of a pill, tablet, capsule, or gel capsule.

5. A method for treating Huntington's disease, comprising:
    administering an effective amount of creatine hydrochloride to a human suffering from Huntington's disease, wherein the effective amount comprises a daily dose of about 2 grams to about 12 grams.

6. The method of claim 5, wherein the creatine hydrochloride is administered in combination with creatinine.

7. The method of claim 5, wherein the creatine hydrochloride is administered in the form of a liquid, gel, or powder.

8. The method of claim 5, wherein after the administering step, spare respiratory capacity of mitochondria in lymphoblast cells increases by at least about 60 percent.

9. The method of claim 5, wherein after the administering step, total ATP turnover of mitochondria in lymphoblast cells increases by at least about 75 percent.

10. A method of treating Huntington's disease or Parkinson's disease in a human, comprising:
    administering to the human a daily dose of a composition comprising creatine hydrochloride, wherein the daily dose comprises about 2 grams to about 12 grams of creatine hydrochloride.

11. The method of claim 10, wherein, after the step of administering, levels of diacylglycerol acyltransferase 2 activity in lymphoblast cells increases by at least about 10 percent.

12. The method of claim 10, wherein the creatine hydrochloride is present in the composition in an amount of at least about 75 percent by weight.

13. The method of claim 10, wherein the daily dose of the composition is administered as a nutritional or dietary supplement or as a functional food.

14. The method of claim 1, wherein the creatine hydrochloride is administered in combination with at least one other compound selected from the group consisting of a homeopathic compound, a co-medication, a nutraceutical, a plant extract, a herbal preparation, a pharmaceutical, and combinations thereof.

15. The method of claim 1, wherein the composition further comprises ethyl (α-guanido-methyl) ethanoate.

16. The method of claim 1, wherein the creatine hydrochloride is present in the composition in an amount of at least about 75 percent by weight of the composition.

17. The method of claim 1, wherein the creatine hydrochloride is present in the composition in an amount of at least about 90 percent by weight of the composition.

18. The method of claim 10, wherein the creatine hydrochloride is present in the composition in an amount of at least about 90 percent by weight of the composition.

* * * * *